United States Patent
Zhang et al.

(10) Patent No.: US 7,078,409 B2
(45) Date of Patent: Jul. 18, 2006

(54) FUSED QUINAZOLINE DERIVATIVES USEFUL AS TYROSINE KINASE INHIBITORS

(75) Inventors: Don Zhang, Old Lyme, CT (US); Guojian Xie, Cheshire, CT (US); Charles Davis, Meriden, CT (US); Zhengzhuang Cheng, New Haven, CT (US); Hang Chen, Waterbury, CT (US); Yinxiang Wang, Cheshire, CT (US); Mehrnaz Kamal, Shelton, CT (US)

(73) Assignee: Beta Pharma, Inc., New Haven, CT (US)

( * ) Notice: Subject to any disclaimer, the term of this patent is extended or adjusted under 35 U.S.C. 154(b) by 210 days.

(21) Appl. No.: 10/397,660

(22) Filed: Mar. 26, 2003

(65) Prior Publication Data

US 2004/0048883 A1    Mar. 11, 2004

Related U.S. Application Data

(60) Provisional application No. 60/368,852, filed on Mar. 28, 2002.

(51) Int. Cl.
*A61K 31/519* (2006.01)
*C07D 239/70* (2006.01)

(52) U.S. Cl. .................. 514/267; 544/249
(58) Field of Classification Search ............ 514/267, 514/211.1, 211.11; 540/467, 468, 484, 546; 544/249
See application file for complete search history.

(56) References Cited

U.S. PATENT DOCUMENTS

| | | | |
|---|---|---|---|
| 5,250,679 A * | 10/1993 | Blackburn et al. | 540/490 |
| 5,403,836 A * | 4/1995 | Blackburn et al. | 514/212.07 |
| 5,457,105 A | 10/1995 | Barker | 514/234.5 |
| 5,569,658 A | 10/1996 | Barker | 514/250 |
| 5,616,582 A | 4/1997 | Barker | 514/234.5 |
| 5,654,307 A * | 8/1997 | Bridges et al. | 514/264.11 |
| 5,747,498 A | 5/1998 | Schnur et al. | 514/259 |
| 6,066,638 A * | 5/2000 | Bereznak et al. | 514/260.1 |
| 6,265,410 B1 | 7/2001 | Bridges et al. | 514/260.1 |
| 6,335,344 B1 | 1/2002 | Schnur | 514/267 |

FOREIGN PATENT DOCUMENTS

| | | |
|---|---|---|
| EP | 1 044 969 A2 | 10/2000 |
| JP | 2000-290262 | 10/2000 |
| WO | WO 95/19970 | 7/1995 |
| WO | WO 96/30347 | 10/1996 |
| WO | WO 97/13760 | 4/1997 |
| WO | WO 97/49688 | 12/1997 |
| WO | WO 99/55683 | 11/1999 |
| WO | WO 01/32155 A2 | 5/2001 |
| WO | WO 01/34574 A1 | 5/2001 |
| WO | WO 01/70255 A2 | 9/2001 |
| WO | WO 02/05791 A2 | 1/2002 |

* cited by examiner

*Primary Examiner*—James O. Wilson
*Assistant Examiner*—Tamthom N. Truong
(74) *Attorney, Agent, or Firm*—Todd E. Garabedian; Elizabeth A. Galletta; Wiggin and Dana LLP

(57) ABSTRACT

The present invention is directed to a compound having the structure

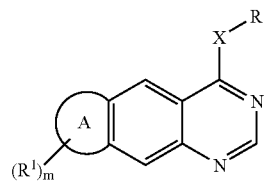

wherein A is a 7–18 membered ring that comprises 0 to 6 heteroatoms selected from O, S, and N; $R^1$ is selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, and substituted or unsubstituted heterocyclyl; m is an integer from 0 to 3; X is selected from the group consisting of $NR^2$, $CHR^3$, O, or S; wherein $R^2$ and $R^3$ are each individually H or $C_{1-8}$alkyl; R is selected from the group consisting of unsubstituted aryl, and substituted or unsubstituted heteroaryl, substituted or unsubstituted aryl-$(C_{1-3})$alkyl, substituted or unsubstituted aryl-$(C_{3-7})$cycloalkyl, substituted or unsubstituted heteroaryl-$(C_{1-3})$alkyl, and substituted or unsubstituted heteroaryl-$(C_{3-7})$cycloalkyl; and pharmaceutically acceptable salts thereof; with the proviso that if A is a 7 or 8 membered ring, then $R^1$ is selected from the group consisting of other than H, $C_1$–$C_4$ alkyl, $(C_1$–$C_4$ alkoxy)$C_1$–$C_4$ alkyl, $C_1$–$C_4$ alkanoyl, $C_1$–$C_4$ alkoxy or —$S(O)_x(C_1$–$C_4$ alkyl) wherein x is 0 to 2, and wherein said alkyl group and the alkyl moieties of said $R^1$ groups are optionally substituted by 1 to 3 halogens. The present invention is also directed to pharmaceutical compositions comprising the above compound, and methods of treating patients suffering from tyrosine kinase-mediated disorders using the above compound.

16 Claims, No Drawings

FUSED QUINAZOLINE DERIVATIVES USEFUL AS TYROSINE KINASE INHIBITORS

This application claims the priority benefit of the U.S. Provisional Application 60/368,852, filed on Mar. 28, 2002.

BACKGROUND OF THE INVENTION

1. Field of the Invention

This invention relates to certain novel fused quinazoline derivatives as tyrosine kinase inhibitors, their synthesis and their use for treating a tyrosine kinase mediated disorder. More particularly, this invention is directed to fused quinazoline derivatives useful as inhibitors of epidermal growth factor receptor (EGFR) tyrosine kinase or vascular endothelial growth factor receptor (VEGFR) tyrosine kinase, methods for producing such compounds and methods for treating a EGFR or VEGFR tyrosine kinase-mediated disorder.

2. Brief Description of the Related Art

Receptor tyrosine kinases are transmembrane proteins involved in signal transduction. They propagate growth factor signals from the cell surface to intracellular processes that control critical functions such as growth, differentiation, angiogenesis and inhibition of apoptosis. In malignancies, these signaling pathways are often exploited to optimize tumor growth and metastasis. One such family of receptor tyrosine kinases is the epidermal growth factor receptor (EGFR) tyrosine kinase. These receptors are overexpressed in a wide variety of major human cancers such as brain, lung, squamous cell, bladder, gastric, breast, head and neck, oesophageal, gynecological and thyroid cancers. Another family of receptor tyrosine kinases is the vascular endothelial growth factor (VEGF) receptor tyrosine kinase. VEGF is an important stimulator of both normal and pathological angiogenesis which has been associated with many cancers and other disorders. Thus, an inhibitor of EGFR or VEGF receptor tyrosine kinase, is useful for treating a variety of human cancers.

U.S. Pat. No. 5,616,582 discloses quinazoline derivatives of the formula below as EGFR inhibitors:

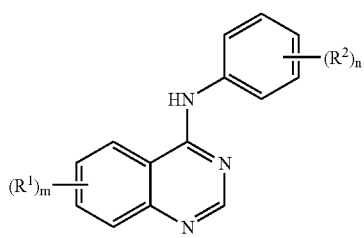

wherein m is 1, 2 or 3 and each $R^1$ includes hydroxy, amino, carboxy, carbamoyl, ureido, (1–4C)alkoxycarbonyl, N(1–4C)alkylcarbamoyi, N,N-di[(1–4C)alkyl]carbamoyl, hydroxyamino, (1–4C)alkylamino, (2–4C)alkanoyloxyamino, trifluoromethoxy, (1–4C)alkyl, (1–4C)alkoxy and (1–3C)alkenedioxy; n is 1 or 2 and each $R^2$ includes; hydrogen, hydroxy, halogeno, trifluoromethyl, amino, nitro, cyano and (1–4C)alkyl.

U.S. Pat. No. 5,569,658 discloses tricyclic derivatives of the formula below as EGFR inhibitors:

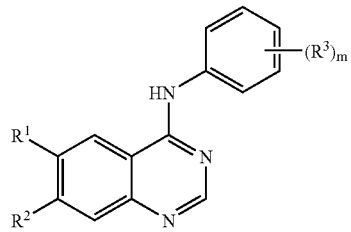

wherein $R^1$ and $R^2$ together form specified optionally substituted groups containing at least one heteroatom so as to form a 5 or 6 membered ring, and $R^3$ includes independently hydrogen, hydroxy, halogeno, (1–4C)alkyl, (1–4C)alkoxy, di-[(1–4C)alky[amino, or (2–4C)alkanoylamino.

WO 95/19970 discloses tricyclic derivatives of the formula below as EGFR inhibitors:

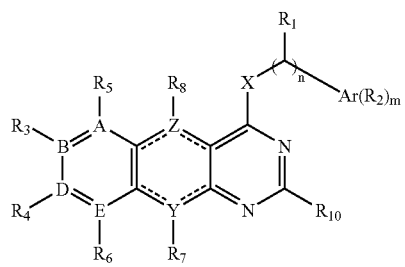

wherein: 1) Y and Z are both C, both N or one N and the other C, in which case the ring structure is a linearly fused 6,6 (5 or 6) tricycle, or 2) one of Y and Z is C=C, C=N, whereupon the other one of Y or Z is simply a bond between the two aromatic rings, then the ring structure is a nonlinear 6,6 (5 or 6) tricycle, or 3) one of Y and Z is N, O or S, whereupon the other one of Y or Z is simply a bond between the two aromatic rings, then the ring structure is a fused 6,5 (5 or 6) tricycle; A, B, D and E can all be carbon, or up to two of them can be nitrogen, whereupon the remaining atoms must be carbon, or any two contiguous positions in A–E can be a single heteroatom, N, O or S, forming a five membered fused ring, in which case one of the two remaining atoms must be carbon, and the other can be either carbon or nitrogen, except that the case where A and B taken together, and D and E taken separately are all three nitrogen atoms; X=O, S, NH or $NR^9$, such that $R^9$=lower alkyl (1–4 carbon atoms), OH, $NH_2$, lower alkoxy (1–4 carbon atoms) or lower monoalkylamino (1–4 carbon atoms); $R^1$=H or lower alkyl; n=0, 1 or 2; Ar is aryl and heteroaryl.

WO 97/13760 discloses tricyclic derivatives of the formula below as EGFR inhibitors:

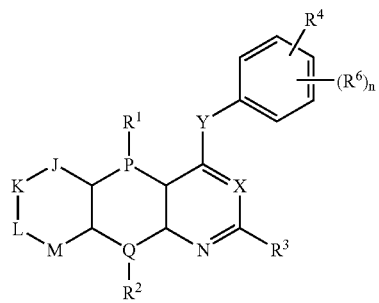

wherein J, K, L and M form a saturated or unsaturated fused ring which is optionally substituted and in which: (i) each of J, K, L and M represent carbon atoms that may be independently replaced by N, O or S; or (ii) any two contiguous positions in J, K, L and M taken together represent a single atom C, N, O or S with at least one of the remaining atoms being carbon and the other being selected from carbon, N, O or S; or (iii) any two contiguous positions in J, K, L and M taken together represent a N atom with the remaining atoms also being N; so that when the fused 5 or 6-membered ring represented by J, K, L and M bears one or two optional substituents in order to satisfy the valency requirements of the atoms in the fused ring and: (i) when the ring atom is carbon, the substituents are independently selected from the group comprising: amino, cyano, halogen, hydroxy, C1–4 alkyl, C1–4 alkoxy, C14 4 alkylthio, C1–4 alkylsulphinyl, C1-4 alkylamino, or (ii) when there are two adjacent carbon atoms in the fused ring, two substituents together form an optionally substituted methylenedioxy or ethylenedioxy group, or (iii) when the ring atom is nitrogen, the substituents are independently selected from the group comprising: C1–4 alkyl, amino C2–4 alkyl, hydroxy C2–4 alkyl and C1–4 alkoxy C2–4 alkyl; subject to the provisos in (i) and (ii) above that the skeleton of the fused heterocyclic ring does not contain more than two atoms selected from O and S, and where the fused ring contains two such atoms said atoms do not occupy adjacent positions in the fused ring; P and O are carbon atoms in an aromatic ring which may be independently replaced to form an aromatic or non-aromatic ring by O, N, S, or a bond; or one of P and Q is C=C or C=N and the other a bond; X is N or CH; Y is a group W(CH$_2$), (CH$_2$)W, or W, in which W is O, S(O)m wherein m is 0, 1 or 2, or NR$^a$ wherein R$^a$ is hydrogen or a C1–8 alkyl group.

U.S. Pat. No. 5,747,498 discloses quinazoline derivatives of the formula below as EGFR inhibitors:

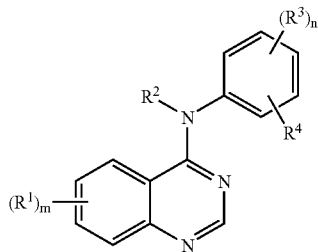

wherein: m is 1, 2, or 3; each R$^1$ is independently selected from the group consisting of hydrogen, halo, hydroxy, hydroxyamino, carboxy, nitro, guanidino, ureido, cyano, trifluoromethyl, and —(C$_1$–C$_4$ alkylene)-W— (phenyl) wherein W is a single bond, O, S or NH; or each R$^1$ is independently selected from R$^9$ and C$_1$–C$_4$ alkyl substituted by cyano, wherein R$^9$ is selected from the group consisting of R$^5$, —OR$^6$, —NR$^6$R$^6$, —C(O)R$^7$, —NHOR$^5$, —OC(O) R$^6$, cyano, A and —YR$^5$; R$^5$ is C$_1$–C$_4$ alkyl; R$^6$ is independently hydrogen or R$^5$; R$^7$ is R$^5$, —OR$^6$ or —NR$^6$R$^6$; A is selected from piperidino, morpholino, pyrrolidino, 4-R$^6$-piperazin-1-yl, imidazol-1-yl, 4-pyridon-1-yl, —(C$_1$–C$_4$ alkylene)(CO$_2$H), phenoxy, phenyl, phenylsulfanyl, C$_2$–C$_4$alkenyl, and —(C$_1$–C$_4$ alkylene)C(O)NR$^6$R$^6$; and Y is S, SO, or SO$_2$; wherein the alkyl moieties in R$^5$, —OR$^6$ and —NR$^6$R$^6$ are optionally substituted by one to three halo substituents and the alkyl moieties in R$^5$, —OR$^6$ and —NR$^6$R$^6$ are optionally substituted by 1 or 2 R$^9$ groups, and wherein the alkyl moieties of said optional substituents are optionally substituted by halo or R$^9$, with the proviso that two heteroatoms are not attached to the same carbon atom; or each R$^1$ is independently selected from —NHSO$_2$R$^5$, phthalimido-(C$_1$–C$_4$)-alkylsulfonylamino, benzamido, benzenesulfonylamino, 3-phenylureido, 2-oxopyrrolidin-1-yl, 2,5-dioxopyrrolidin-1-yl, and R$^{10}$—(C$_2$–C$_4$)-alkanoylamino wherein R$^{10}$ is selected from halo, —OR$^6$, C$_2$–C$_4$ alkanoyloxy, —C(O)R$^7$, and —NR$^6$R$^6$; and wherein said —NHSO$_2$R$^5$, phthalimido-(C$_1$–C$_4$-alkylsulfonylamino, benzamido, benzenesulfonylamino, 3-phenylureido, 2-oxopyrrolidin-1-yl, 2,5-dioxopyrrolidin-1-yl, and R$^{10}$—(C$_2$–C$_4$)-alkanoylamino R$^1$ groups are optionally substituted by 1 or 2 substituents independently selected from halo, C$_1$–C$_4$alkyl, cyano, methanesulfonyl and C$_1$–C$_4$ alkoxy; or two R$^1$ groups are taken together with the carbons to which they are attached to form a 5–8 membered ring that includes 1 or 2 heteroatoms selected from O, S and N; R$^2$ is hydrogen or C$_1$–C$_6$ alkyl optionally substituted by 1 to 3 substituents independently selected from halo, C$_1$–C$_4$ alkoxy, —NR$^6$R$^6$, and —NHSO$_2$R$^5$; n is 1 or 2 and each R$^3$ is independently selected from hydrogen, halo, hydroxy, C$_1$–C$_6$ alkyl, —NR$^6$R$^6$, and C$_1$–C$_4$ alkoxy, wherein the alkyl moieties of said R$^3$ groups are optionally substituted by 1 to 3 substituents independently selected from halo, C$_1$–C$_4$ alkoxy, —NR$^6$R$^6$, and —NHSO$_2$R$^5$; and, R$^4$ is azido or —(ethynyl)-R$^{11}$ wherein R$^{11}$ is hydrogen or C$_1$–C$_6$ alkyl optionally substituted by hydroxy, —OR$^6$, or —NR$^6$R$^6$.

WO 97/49688 discloses tricyclic derivatives of the formula below as EGFR inhibitors:

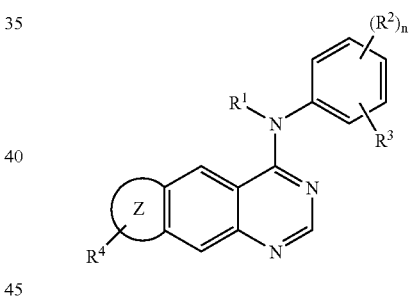

wherein: n is 0 to 2; R$^1$ is hydrogen or C1–C6 alkyl optionally substituted by 1 to 3 substituents independently selected from the group consisting of halo, C1–C4 alkoxy, —NR$^6$R$^7$, and —SO$_2$R$^5$; each R$^2$ is independently selected from the group consisting of halo, hydroxy, C1–C6 alkyl, —NR$^6$R$^7$, and C1–C4 alkoxy, wherein said alkyl group and the alkyl moieties of said R$^2$ groups are optionally substituted by 1 to 3 substituents independently selected from the group consisting of halo, C1–C4 alkoxy, —NR$^6$R$^7$ and —SO$_2$R$^5$; R$^3$ is azido or —(ethynyl)-R$^8$ wherein R$^8$ is hydrogen or C1–C6 alkyl optionally substituted by hydroxy, —OR$^6$, or —NR$^6$R$^7$; R$^4$ is H, C1–C4 alkyl, (C1–C4 alkoxy) C1–C4 alkyl, C1–C4 alkanoyl, C1–C4 alkoxy or —S(O)$_x$ (C1–C4 alkyl) wherein x is 0 to 2, and wherein said alkyl group and the alkyl moieties of said R$^4$ groups are optionally substituted by 1 to 3 halogens; each R$^5$ is C1–C4 alkyl optionally substituted by 1 to 3 halogens; R$^6$ and R$^7$ are independently selected from hydrogen and R$^5$; and, Z is a 5 to 8 membered fused ring that includes 0 to 3 heteroatoms selected from O, S and N.

SUMMARY OF THE INVENTION

In one aspect the present invention is directed to compounds having the general structure

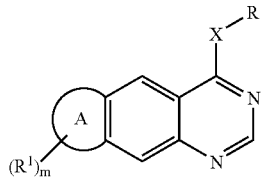

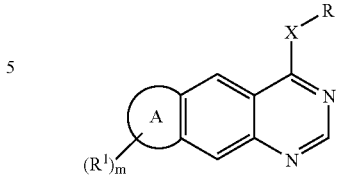

wherein A is a 7–18 membered ring; $R^1$ is selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulphinyl, $C_{1-8}$alkylsulphonyl, arylsulphonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl)carbamoyl, N,N-di-($C_{1-8}$alkyl) carbamoyl, $C_{1-8}$alkanoyloxy, $C_{1-8}$alkanoylamino, $C_{3-8}$alkynoylamino, N—($C_{1-8}$alkyl)sulphamoyl, and N,N-di-($C_{1-8}$alkyl)sulphamoyl; m is an integer from 0 to 3; X is selected from the group consisting of $NR^2$, $CHR^3$, O, or S; wherein $R^2$ and $R^3$ are each individually H or $C_{1-8}$alkyl; R is selected from the group consisting of substituted or unsubstituted aryl, substituted or unsubstituted heteroaryl, substituted or unsubstituted aryl-($C_{1-3}$)alkyl, substituted or unsubstituted aryl-($C_{3-7}$)cycloalkyl, substituted or unsubstituted heteroaryl-($C_{1-3}$)alkyl, and substituted or unsubstituted heteroaryl-($C_{3-7}$)cycloalkyl; and pharmaceutically acceptable salts thereof; with the proviso that if A is a 7 or 8 membered ring, then $R^1$ is selected from the group consisting of other than H, $C_1$–$C_4$ alkyl, ($C_1$–$C_4$ alkoxy)$C_1$–$C_4$ alkyl, $C_1$–$C_4$ alkanoyl, $C_1$–$C_4$ alkoxy or —S(O)$_x$($C_1$–$C_4$ alkyl) wherein x is 0 to 2, and wherein said alkyl group and the alkyl moieties of said $R^1$ groups are optionally substituted by 1 to 3 halogens.

In another aspect, the present invention is directed to a pharmaceutical composition, comprising: the above compound and a pharmaceutically acceptable carrier.

In another aspect, the present invention is directed to a method of treating a patient suffering from tyrosine kinase-mediated disorders, comprising the step of administering to said patient a therapeutically effective amount of the compound of the above compound.

These and other aspects will become apparent from the following written description of the invention.

DETAILED DESCRIPTION OF THE INVENTION

The present invention is directed to novel compounds having tyrosine kinase inhibitory activity. The compounds of the invention have the general structure In particular, the compounds of the invention are useful in treating epidermal growth factor receptor (EGFR) tyrosine kinase or vascular endothelial growth factor receptor (VEGFR) tyrosine kinase-mediated disorders in a subject in need thereof. In general, such disorders manifest themselves in the form of cancers, such as brain, lung, squamous cell, bladder, gastric, pancreatic, breast, head, neck, oesophageal, prostate, colorectal, gynecological or thyroid cancers.

As defined herein, the term "subject" refers to an animal, preferably a mammal, most preferably a human, who has been the object of treatment, observation or experiment. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "substituted", as defined herein, includes multiple substituents (e.g., Phe, aryl, heteroalkyl, heteroaryl), preferably from one to five substituents, more preferably from one to three substituents, most preferably from one to two substituents, independently selected from the list of substituents.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The term "halo" or "halogen", as used herein, unless otherwise indicated, means fluoro, chloro, bromo or iodo. Preferred halo groups are fluoro, chloro and bromo.

As used herein, unless otherwise indicated, alkyl includes saturated monovalent hydrocarbon radicals having straight, branched or cyclic moieties. For example, alkyl radicals include methyl, ethyl, propyl, isopropyl, cyclcopropyl, n-butyl, isobutyl, sec-butyl, t-butyl, cyclcobutyl, n-pentyl, 3-(2-methyl)butyl, 2-pentyl, 2-methylbutyl, neopentyl, cyclcopentyl, n-hexyl, 2-hexyl, 2-methylpentyl and cyclohexyl. Alkoxy radicals are oxygen ethers formed from the previously described straight, branched chain or cyclic alkyl groups. Similarly, alkenyl and alkynyl groups include straight, branched chain or cyclic alkenes and alkynes. The term "hydroxyalkyl" refers to radicals wherein the alkyl chain terminates with a hydroxy radical of the formula HO-alkyl. The term aminoalkyl refers to an alkyl group substituted with an amino group (i.e., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (i.e., —N-$[alkyl]_2$).

The term "aryl", as used herein, unless otherwise indicated, refers to an unsubstituted or substituted aromatic group such as phenyl, naphthyl and anthracenyl. The term "aroyl" refers to the group —C(O)-aryl.

The term "heterocyclyl", as used herein, unless otherwise indicated, represents an unsubstituted or substituted stable three to eight membered monocyclic saturated ring system which consists of carbon atoms and from one to three heteroatoms selected from N, O or S, and wherein the nitrogen or sulfur heteroatoms may optionally be oxidized, and the nitrogen heteroatom may optionally be quaternized. The heterocyclyl group may be attached at any heteroatom or carbon atom which results in the creation of a stable structure. Examples of such heterocyclyl groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an unsubstituted or substituted stable five or six membered monocyclic aromatic ring system or an unsubstituted or substituted nine or ten membered benzo-fused heteroaromatic ring system or bicyclic heteroaromatic ring system which consists of carbon atoms and from one to four heteroatoms selected from N, O or S, and wherein the nitrogen or sulfur heteroatoms may optionally be oxidized, and the nitrogen heteroatom may optionally be quaternized. The heteroaryl group may be attached at any heteroatom or carbon atom which results in the creation of a stable structure. Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "arylalkyl" means an alkyl group substituted with one or more aryl groups. The "arylalkenyl" or "arylalkynyl" indicates an alkenyl or alkynyl group substituted with one or more aryl groups. Similarly, the "heteroarylalkyl", "heteroarylalkenyl" or "heteroarylalkynyl" means an alkyl, alkenyl or alkynyl group substituted with one or more heteroaryl groups, and heterocyclylalkyl", "heterocyclylalkenyl" or "heterocyclylalkynyl" means an alkyl, alkenyl or alkynyl group substituted with one or more heterocyclyl groups.

The term "carbonyl" refers to the group C(O).

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$–$C_6$) shall refer independently to the number of carbon atoms in an alkyl moiety or to the alkyl portion of a larger substituent in which alkyl appears as its prefix root.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

As indicated above, the present invention is directed to compounds having the general structure

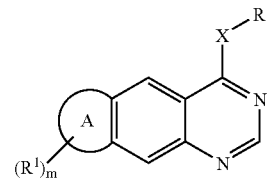

wherein A is a 7–18 membered ring; $R^1$ is selected from the group consisting of hydrogen, halogen, substituted or unsubstituted $C_{1-8}$alkyl, substituted or unsubstituted $C_{2-8}$alkenyl, substituted or unsubstituted $C_{2-8}$alkynyl, substituted or unsubstituted aryl, substituted or unsubstituted heteroaryl, substituted or unsubstituted heterocyclyl, $C_{1-8}$alkanoyl, $C_{1-8}$alkoxycarbonyl, $C_{1-8}$alkylsulphinyl, $C_{1-8}$alkylsulphonyl, arylsulphonyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N—($C_{1-8}$alkyl)carbamoyl, N,N-di-($C_{1-8}$alkyl)carbamoyl, $C_{1-8}$alkanoyloxy, $C_{1-8}$alkanoylamino, $C_{3-8}$alkynoylamino, N-($C_{1-8}$alkyl)sulphamoyl, and N,N-di-($C_{1-8}$alkyl)sulphamoyl; m is an integer from 0 to 3; X is selected from the group consisting of $NR^2$, $CHR^3$, O, or S; wherein $R^2$ and $R^3$ are each individually H or $C_{1-8}$alkyl; R is selected from the group consisting of substituted or unsubstituted aryl, substituted or unsubstituted heteroaryl, substituted or unsubstituted aryl-$(C_{1-3})$alkyl, substituted or unsubstituted aryl-$(C_{3-7})$cycloalkyl, substituted or unsubstituted heteroaryl-$(C_{1-3})$alkyl, and substituted or unsubstituted heteroaryl-$(C_{3-7})$cycloalkyl; and pharmaceutically acceptable salts thereof; with the proviso that if A is a 7 or 8 membered ring, then $R^1$ is selected from the group consisting of other than H, $C_1$–$C_4$ alkyl, $(C_1$–$C_4$ alkoxy$)C_1$–$C_4$ alkyl, $C_1$–$C_4$ alkanoyl, $C_1$–$C_4$ alkoxy or —$S(O)_x(C_1$–$C_4$ alkyl) wherein x is 0 to 2, and wherein said alkyl group and the alkyl moieties of said $R^1$ groups are optionally substituted by 1 to 3 halogens.

In one preferred embodiment, ring A further comprises that 0 to 6 heteroatoms selected from the group consisting of O, S, and N.

In a preferred embodiment, $R^1$ is selected from the group consisting hydrogen, halogen, $C_{1-8}$alkyl, $C_{2-8}$alkenyl, $C_{2-8}$alkynyl, aryl, heteroaryl, heterocyclyl, (halo)$_{1-3}(C_{1-8})$alkyl, hydroxy$(C_{1-8})$alkyl, $C_{1-4}$alkoxy$(C_{1-8})$alkyl, cyano $(C_{1-8})$ alkyl, amino$(C_{1-8})$alkyl, aryl$(C_{1-8})$alkyl, heteroaryl $(C_{1-8})$alkyl, heterocyclyl$(C_{1-8})$alkyl, (halo)$_{1-3}(C_{2-8})$alkenyl, hydroxy$(C_{2-8})$alkenyl, $C_{1-4}$alkoxy$(C_{2-8})$alkenyl, cyano $(C_{2-8})$ alkenyl, and amino$(C_{2-8})$alkenyl, aryl$(C_{2-8})$alkenyl, heteroaryl$(C_{2-8})$alkenyl, heterocyclyl$(C_{2-8})$alkenyl, (halo)$_{1-3}$ $(C_{2-8})$alkynyl, hydroxy$(C_{2-8})$alkynyl, $C_{1-4}$alkoxy$(C_{2-8})$alkynyl, cyano$(C_{2-8})$alkynyl, amino$(C_{2-8})$alkynyl, aryl$(C_{2-8})$alkynyl, heteroaryl$(C_{2-8})$alkynyl, heterocyclyl$(C_{2-8})$alkynyl, $C_{1-8}$alkanoyl, aryl$(C_{1-8})$alkanoyl, heteroaryl $(C_{1-8})$alkanoyl, heterocyclyl$(C_{1-8})$alkanoyl, $C_{1-8}$alkoxycarbonyl, aryl$(C_{1-8})$alkoxycarbonyl, heteroaryl$(C_{1-8})$alkoxycarbonyl, heterocyclyl$(C_{1-8})$alkoxycarbonyl, $C_{1-8}$alkylsulphinyl, $C_{1-8}$alkylsulphonyl, arylsulphonyl, aryl$(C_{1-8})$alkylsulphonyl, heteroaryl $(C_{1-8})$alkylsulphonyl, heterocyclyl$(C_{1-8})$alkylsulphonyl, aryl, heteroaryl, heterocyclyl, cyano, nitro, hydroxy, amino, carboxy, oxo, carbamoyl, $C_{1-8}$alkoxy, $C_{2-8}$alkenyloxy, $C_{2-8}$alknyloxy, $C_{1-8}$alkylthio, N-$(C_{1-8}$alkyl)carbamoyl, N,N-di-$(C_{1-8}$alkyl)carbamoyl, $C_{1-8}$alkanoyloxy, $C_{1-8}$alkanoylamino, $C_{3-8}$alkynoylamino, N-$(C_{1-8}$alkyl)sulphamoyl, and N,N-di-$(C_{1-8}$alkyl)sulphamoyl.

In another preferred embodiment, the above amino, amino$(C_{1-8})$alkyl, amino$(C_{2-8})$alkenyl or amino$(C_{2-8})$alkynyl within $R^1$ is substituted with two substituents independently selected from the group consisting of hydrogen, $C_{1-8}$alkyl, $C_{2-8}$alkenyl, $C_{2-8}$alkynyl.

In another preferred embodiment, any aryl, heteroaryl or heterocyclyl group within $R^1$ optionally bears one to three substituents independently selected from halogeno, trifluoromethyl, cyano, nitro, hydroxy, amino, carboxy, carbamoyl, $(C_{1-8})$alkyl, $(C_{2-8})$alkenyl, $(C_{2-8})$alkynyl, $(C_{1-8})$alkoxy.

In addition, the aryl or heteroaryl group of R may each optionally be substituted with one to three substituents independently selected from the group consisting of halogen, $C_{1-8}$alkyl, $C_{2-8}$alkenyl, $C_{2-8}$alkynyl, cyano, nitro, hydroxy, amino, carboxy, carbamoyl, $C_{1-8}$alkoxy, $C_{2-8}$alkenyloxy, $C_{2-8}$alknyloxy, $C_{1-8}$alkylthio, $C_{1-8}$alkylsulphinyl, $C_{1-8}$alkylsulphonyl, $C_{1-8}$alkoxycarbonyl, N-$(C_{1-8}$alkyl)carbamoyl, N,N-di-$(C_{1-8}$alkyl)carbamoyl, (halo)$_{1-3}(C_{1-8})$alkyl-, (halo)$_{1-3}(C_{1-8})$alkoxy-, hydroxy$(C_{1-8})$alkyl, $C_{1-4}$alkoxy $(C_{1-8})$alkyl, cyano$(C_{1-8})$alkyl, amino$(C_{1-8})$alkyl, aryl, aryl $(C_{1-8})$alkyl, heteroaryl, heteroaryl$(C_{1-8})$alkyl, heterocyclyl, heterocyclyl$(C_{1-8})$alkyl, $C_{2-8}$alkanoyl, $C_{2-8}$alkanoyloxy, $C_{2-8}$alkanoylamino, $C_{3-8}$alkenoylamino, $C_{3-8}$alkynoylamino, N-$(C_{1-8}$alkyl)sulphamoyl, N.,N-di-$(C_{1-8}$alkyl)sulphamoyl, $C_{1-8}$alkanesulphonylamino, $(C_{1-3})$alkylenedioxy, or from a group of the formula:

—Y—$R^4$ wherein Y is selected from O, S, N($R^5$), SO, $SO_2$, CO, CON($R^5$), N($R^5$)CO, $SO_2$N($R^5$), N($R^5$)$SO_2$, wherein $R^5$ is hydrogen or $(C_{1-4})$alkyl, and $R^4$ is halogeno-$(C_{1-8})$alkyl, hydroxy-$(C_{1-8})$alkyl, $(C_{1-4})$alkoxy-$(C_{1-8})$alkyl, cyano-$(C_{1-8})$ alkyl, amino-$(C_{1-8})$alkyl, $(C_{1-8})$alkylamino-$(C_{1-8})$alkyl or di-[$(C_{1-8})$alkyl]amino-$(C_{1-8})$alkyl, aryl, aryl-$(C_{1-8})$alkyl, heteroaryl, heteroaryl-$(C_{1-8})$alkyl, heterocyclyl or heterocyclyl-$(C_{1-8})$alkyl.

The above amino or amino$(C_{1-8})$alkyl group within a substituent on R is substituted with two substituents independently selected from the group consisting of hydrogen, $C_{1-8}$alkyl, $C_{2-8}$alkenyl, and $C_{2-8}$alkynyl.

The above aryl, heteroaryl or heterocyclyl group within a substituent on R optionally bears one to three substituents independently selected from the group consisting of halogen, trifluoromethyl, cyano, nitro, hydroxy, amino, carboxy, carbamoyl, $(C_{1-8})$alkyl, $(C_{2-8})$alkenyl, $(C_{2-8})$alkynyl, and $(C_{1-8})$alkoxy.

In one preferred embodiment, R is aryl and heteroaryl.

In another preferred embodiment, ring A is a 9–18 membered ring that includes 1 to 6 heteroatoms selected from O, S, and N, and more preferably a 9–15 membered ring that includes 2 to 5 heteroatoms selected from O, S, and N. In a further preferred embodiment, m is 0 to 2.

In another preferred embodiment, X is $NR^2$; and $R^2$ is H or $C_{1-4}$alkyl.

More preferably, R is phenyl, wherein phenyl is optionally substituted with one to three substituents independently selected from the group consisting of halogen, $C_{1-4}$alkyl, $C_{2-4}$alkenyl, $C_{2-4}$alkynyl, cyano, nitro, hydroxy, amino (substituted with hydrogen or $C_{1-4}$alkyl), carboxy, carbamoyl, $C_{1-4}$alkoxy, $C_{1-4}$alkylthio, $C_{1-4}$alkylsulphinyl, $C_{1-4}$alkylsulphonyl, $C_{1-4}$alkoxycarbonyl, N-$(C_{1-4}$alkyl)carbamoyl, N,N-di-$(C_{1-4}$alkyl)carbamoyl, (halo)$_{1-3}(C_{1-4})$alkyl-, (halo)$_{1-3}$ $(C_{1-4})$alkoxy-, hydroxy$(C_{1-4})$alkyl, $C_{1-4}$alkoxy$(C_{1-4})$alkyl, cyano$(C_{1-4})$alkyl, amino$(C_{1-4})$alkyl (wherein amino is substituted with two substituents independently selected from the group consisting of hydrogen, $C_{1-4}$alkyl, $C_{2-4}$alkenyl, $C_{2-4}$alkynyl), aryl, aryl$(C_{1-4})$alkyl, heteroaryl, heteroaryl $(C_{1-4})$alkyl, heterocyclyl, heterocyclyl$(C_{1-4})$alkyl, $C_{2-4}$alkanoyl, $C_{2-4}$alkanoyloxy, $C_{2-4}$alkanoylamino, N-$(C_{1-4}$alkyl) sulphamoyl, N.,N-di-$(C_{1-4}$alkyl)sulphamoyl, $C_{1-4}$alkanesulphonylamino, $(C_{1-3})$alkylenedioxy, or from a group of the formula:

—Y—$R^4$ wherein Y is selected from O, S, N($R^5$), SO, $SO_2$, CO, CON($R^5$), N($R^5$)CO, $SO_2$N($R^5$), N($R^5$)$SO_2$, wherein $R^5$ is hydrogen or $(C_{1-4})$alkyl, and $R^4$ is halogeno-$(C_{1-4})$alkyl, hydroxy-$(C_{1-4})$alkyl, $(C_{1-4})$alkoxy-$(C_{1-4})$alkyl, cyano-$(C_{1-4})$ alkyl, amino-$(C_{1-4})$alkyl, $(C_{1-4})$alkylamino-$(C_{1-4})$alkyl or di-[$(C_{1-4})$alkyl]amino-$(C_{1-4})$alkyl, aryl, aryl-$(C_{1-4})$alkyl, heteroaryl, heteroaryl-$(C_{1-4})$alkyl, heterocyclyl or heterocyclyl-$(C_{1-4})$alkyl, and wherein any aryl, heteroaryl or heterocyclyl group within a substituent on R optionally bears one to three substituents independently selected from halogeno, trifluoromethyl, cyano, nitro, hydroxy, amino, carboxy, carbamoyl, $(C_{1-4})$alkyl, $(C_{2-4})$alkenyl, $(C_{2-4})$alkynyl, $(C_{1-4})$alkoxy;

Preferred embodiments of the present invention include compounds of Formula (I) wherein, $R^1$ is hydrogen, halogen, $C_{1-4}$alkyl, $C_{2-4}$alkenyl, $C_{2-4}$alkynyl, aryl, heteroaryl, heterocyclyl, (halo)$_{1-3}(C_{1-4})$alkyl, hydroxy$(C_{1-4})$alkyl, $C_{1-4}$alkoxy$(C_{1-4})$alkyl, cyano$(C_{1-4})$alkyl, amino$(C_{1-4})$alkyl (wherein amino is substituted with two substituents independently selected from the group consisting of hydrogen, $C_{1-4}$alkyl, $C_{2-4}$alkenyl, $C_{2-4}$alkynyl), aryl($C_{1-4}$)alkyl, heteroaryl($C_{1-4}$)alkyl, heterocyclyl($C_{1-4}$)alkyl, (halo)$_{1-3}$($C_{2-4}$) alkenyl, hydroxy($C_{2-4}$)alkenyl, $C_{1-4}$alkoxy($C_{2-4}$)alkenyl, cyano($C_{2-4}$)alkenyl, amino($C_{2-4}$)alkenyl (wherein amino is substituted with two substituents independently selected from the group consisting of hydrogen, $C_{1-4}$alkyl, $C_{2-4}$alkenyl, $C_{2-4}$alkynyl), aryl($C_{2-4}$)alkenyl, heteroaryl($C_{2-4}$)alkenyl, heterocyclyl($C_{2-4}$)alkenyl, (halo)$_{1-3}$($C_{2-4}$)alkynyl, hydroxy($C_{2-4}$)alkynyl, $C_{1-4}$alkoxy($C_{2-4}$)alkynyl, cyano ($C_{2-4}$)alkynyl, amino($C_{2-4}$)alkynyl (wherein amino is substituted with two substituents independently selected from the group consisting of hydrogen, $C_{1-4}$alkyl, $C_{2-4}$alkenyl, $C_{2-4}$alkynyl), aryl($C_{2-4}$)alkynyl, heteroaryl($C_{2-4}$)alkynyl, heterocyclyl($C_{2-4}$)alkynyl, $C_{1-4}$alkanoyl, aryl($C_{1-4}$)alkanoyl, heteroaryl($C_{1-4}$)alkanoyl, heterocyclyl($C_{1-4}$)alkanoyl, $C_{1-4}$alkoxycarbonyl, aryl($C_{1-4}$)alkoxycarbonyl, heteroaryl ($C_{1-4}$)alkoxycarbonyl, heterocyclyl($C_{1-4}$)alkoxycarbonyl, $C_{1-4}$alkylsulphinyl, $C_{1-4}$alkylsulphonyl, aryl($C_{1-4}$)alkylsulphonyl, heteroaryl($C_{1-4}$)alkylsulphonyl, heterocyclyl($C_{1-4}$) alkylsulphonyl, cyano, nitro, hydroxy, amino (substituted with two substituents independently selected from the group consisting of hydrogen, $C_{1-4}$alkyl, $C_{2-4}$alkenyl, $C_{2-4}$alkynyl), carboxy, carbamoyl, $C_{1-4}$alkoxy, $C_{2-4}$alkenyloxy, $C_{2-4}$alknyloxy, $C_{1-4}$alkylthio, N-($C_{1-4}$alkyl)carbamoyl, N,N-di-($C_{1-4}$alkyl)carbamoyl, $C_{1-4}$alkanoyloxy, $C_{1-4}$alkanoylamino, $C_{3-6}$alkynoylamino, N-($C_{1-4}$alkyl)sulphamoyl, N,N-di-($C_{1-4}$alkyl)sulphamoyl, and wherein any aryl, heteroaryl or heterocyclyl group within $R^1$ optionally bears one to three substituents independently selected from halogeno, trifluoromethyl, cyano, nitro, hydroxy, amino, carboxy, carbamoyl, ($C_{1-4}$)alkyl, ($C_{2-4}$)alkenyl, ($C_{2-4}$)alkynyl, ($C_{1-4}$) alkoxy;

More preferably, $R^1$ is selected from the group consisting of hydrogen, halogen, $C_{1-4}$alkyl, $C_{2-4}$alkenyl, $C_{2-4}$alkynyl, aryl, heteroaryl, heterocyclyl, (halo)$_{1-3}$($C_{1-4}$)alkyl, hydroxy ($C_{1-4}$)alkyl, $C_{1-4}$alkoxy($C_{1-4}$)alkyl, cyano($C_{1-4}$)alkyl, amino ($C_{1-4}$)alkyl (wherein amino is substituted with hydrogen or $C_{1-4}$alkyl), aryl($C_{1-4}$)alkyl, heteroaryl($C_{1-4}$)alkyl, heterocyclyl($C_{1-4}$)alkyl, hydroxy, amino (substituted with hydrogen or $C_{1-4}$alkyl), carboxy, $C_{1-4}$alkoxy, $C_{1-4}$alkylthio, and wherein any aryl, heteroaryl or heterocyclyl group within $R^1$ optionally bears one to three substituents independently selected from halogen, trifluoromethyl, cyano, nitro, hydroxy, amino, carboxy, carbamoyl, ($C_{1-4}$)alkyl, ($C_{2-4}$) alkenyl, ($C_{2-4}$)alkynyl, ($C_{1-4}$)alkoxy; and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts." The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

In general, the compounds of the present invention can be prepared according to Scheme 1. The 6,7-dihydroxyquinazoline intermediates 6 can be prepared following the published procedures (Bridges et al., *J. Med. Chem.* 1996, 39, 267–276 and Barker, U.S. Pat. No. 5,616,582, 1997). Treatment of 6 with an appropriate unsubstituted or substituted bis-alkylating agent 7 and a base such as potassium carbonate in a dipolar aprotic solvent such as DMF provideds 6,7-fused quinazoline derivatives 8.

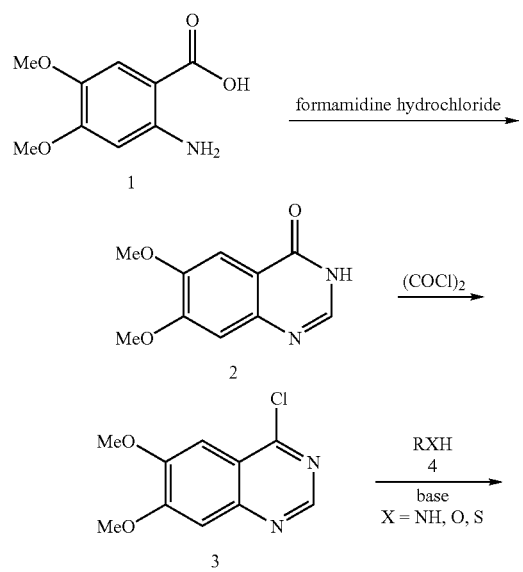

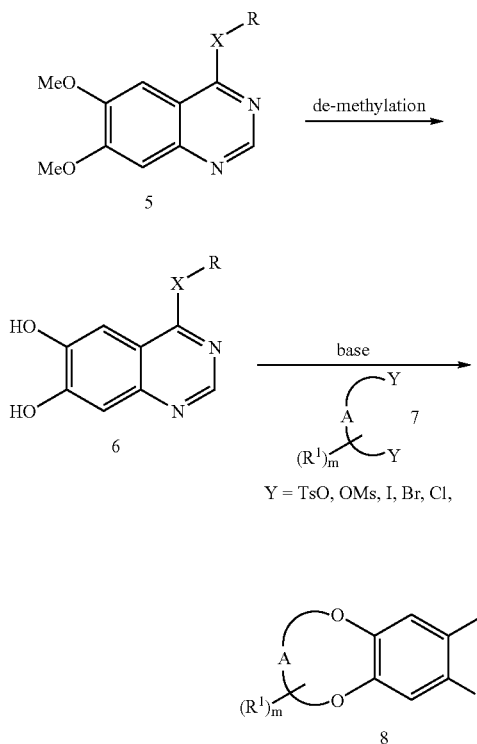

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene & P. G. M. Wuts, *Protective Groups in Organic Synthesis,* John Wiley & Sons, 1991. The protecting groups may be removed at a convenient subsequent stage using methods known in the art.

Administration of the active compounds can be effected by any method which enables delivery of the compounds to the site of action (e.g., cancer cells). These methods include oral routes, rectal routes, intraduodenal routes, parenteral injection (including intravenous, subcutaneous, intramuscular, intravascular or infusion), topical administration, etc. The amount of active compound administered will, of course, be dependent on the subject being treated, on the severity of the affliction, on the manner of administration and on the judgement of the prescribing physician. However an effective dosage is in the range of approximately 0.001 mg to about 300 mg (preferably, from about 0.01 mg to about 100 mg; and, more preferably, from about 0.1 mg to about 30 mg) and may be given at a dosage of from about 0.001 mg/kg/day to about 300 mg/kg/day (preferably, from about 0.01 mg/kg/day to about 100 mg/kg/day; and, more preferably, from about 0.1 mg/kg/day to about 30 mg/kg/day).

The composition may, for example, be in a form suitable for oral administration such as a tablet, capsule, pill, powder, sustained release formulation, solution, or suspension; for parenteral injection such as a sterile solution, suspension or emulsion; or for topical administration such as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the present invention as an active ingredient. In addition, it may include other medicinal or pharmaceutical agents, carriers, adjuvants, etc.

Exemplary parenteral administration forms include solutions or suspensions of active compounds in sterile aqueous solutions, for example aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

An example of use of the invention is a method of treating a epidermal growth factor receptor (EGFR) tyrosine kinase or vascular endothelial growth factor receptor (VEGFR) tyrosine kinase mediated disorder in a subject in need thereof comprising administering to the subject a therapeutically effective amount of any of the compounds or pharmaceutical compositions described above. In a preferred embodiment, the method relates to the treatment of cancer such as brain, lung, squamous cell, bladder, gastric, pancreatic, breast, head, neck, oesophageal, prostate, colorectal, gynecological or thyroid cancer.

EXAMPLES

The following Examples are provided to better illustrate the present invention. All parts and percentages are by weight and all temperatures are degrees Celsius, unless explicitly stated otherwise. The following abbreviations have been used in the examples: ATP, Adenosine triphosphate; DMF, N,N-Dimethylformamide; DMSO, Dimethyl sulfoxide; EtOAc, Ethyl acetate; GSR, Glutathione-S-Transferase; Crk, CT10 (Chicken Tumor Retrovirus 10); min, Minute; h, Hour; rt, room temperature; SDS, Sodium Dodecyl Sulfate; SDS-PAGE, Sodium Dodecyl Sulfate PolyAcrylamide Electrophoresis Gel; TLC, Thin layer chromatography.

All chemicals were purchased from commercial suppliers and used without further purification. TLC was performed with Whatman 250-μm silica gel plates. Preparative TLC was performed with Analtech 1000-μm silica gel GF plates. Flash column chromatography was conducted with flash column silica gel (40–63 m) and column chromatography was conducted with standard silica gel. Nuclear magnetic resonance (NMR) spectra were recorded on a QE-GE-Plus300 spectrometer with $Me_4Si$ as an internal standard (s=singlet, d=doublet, t=triplet, br=broad). Mass spectra (MS) were recorded on a LCMS-2010 (Shmadzu) mass spectrometer.

Example 1

(3-Bromo-phenyl)-(7,8,10,11-tetrahydro-6,9,12-trioxa-1,3-diaza-cyclonona[b]naphthalen-4-yl)-amine (Compound 9)

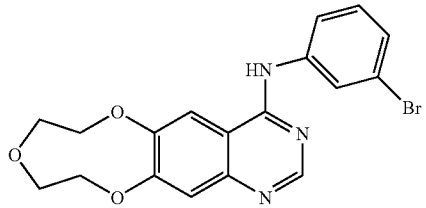

9

A mixture of 6,7-dihydroxy-4-(3'-bromoanilino)quinazoline (50 mg, 0.15 mmol, prepared according to published procedures), potassium carbonate (83 mg, 0.60 mmol) in DMF (13 mL) was stirred at 80° C. for 10 min, to which was then added dropwise a solution of bis diethleneglycol-OTs (62 mg, 0.15 mmol) in DMF (2 mL) over 30 min. The reaction mixture was then stirred at 80° C. for 1.5 h, at which time TLC indicated that the reaction had been completed. DMF was removed in vacuo and the residue was partitioned between EtOAc (60 mL) and water (30 mL). The organic phase was separated, washed with 10% $Na_2CO_3$ (20 mL), brine (20 mL), dried over $Na_2SO_4$, and evaporated in vacuo to give a solid. The crude product was purified by silica gel flash chromatography ($CH_2Cl_2$/MeOH, 97:2) to afford Compound 9 as a gray solid (25 mg). For free base: $^1H$ NMR (DMSO-$d_6$) δ 8.53 (s, 1H), 8.24 (m, 2H), 7.91 (d, J=8.3 Hz, 1H), 7.38–7.26 (m, 3H), 4.58 (m, 2H), 4.42 (m, 2H), 3.87 (m, 4H). ES-MS m/z 402 (MH$^+$). To convert the free base to its HCl salt, the free base was dissolved in HCl/CHCl$_3$ (1:1), and to the solution was then added 1.0 N HCl in ether. The resulting solid was collected by filtration, washed with ether to give the HCl salt of Compound 9 as a light yellow solid.

Example 2

(3-Bromo-phenyl)-(7,8,10,11,13,14-hexahydro-6,9,12,15-tetraoxa-1,3-diaza-cyclododeca[b]naphthalen-4-yl)-amine (Compound 10)

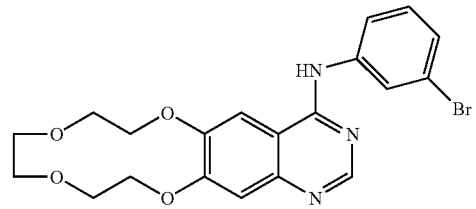

10

Following the same procedure as described in Example 1, Compound 10 was prepared. For free base: $^1H$ NMR (DMSO-$d_6$) δ 8.55 (s, 1H), 8.20 (t, J=1.8 Hz, 1H), 8.14 (s, 1H), 7.89 (d, J=8.0 Hz, 1H), 7.38–7.27 (m, 3H), 4.30 (m, 4H), 3.82–3.76 (m, 4H), 3.64 (s, 4H). ES-MS m/z 446 (MH$^+$). The product was converted to its HCl salt as described in Example 1.

Example 3

(3-Bromo-phenyl)-(2,5,8,11,14-pentaoxa-18,20-diaza-tricyclo[13.8.0.0$^{17,22}$]tricosa-1(15),16,18,20,22-pentaen-21-yl)-amine (Compound 11)

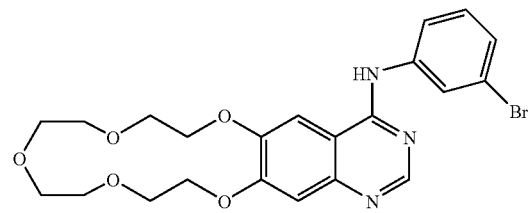

11

Following the same procedure as described in Example 1, Compound 11 was prepared and converted to its HCl salt. For HCl salt: $^1H$ NMR (DMSO-$d_6$) δ 8.87 (s, 1H), 8.23 (s, 1H), 8.02 (d, J=1.8 Hz, 1H), 7.75 (d, J=7.7 Hz, 1H), 7.52–7.43 (m, 2H), 7.26 (s, 1H), 4.28 (m, 4H), 3.88 (m, 4H), 3.47 (m, 8H). ES-MS m/z 490 (MH$^+$).

Example 4

(3-Bromo-phenyl)-[9-(toluene-4-sulfonyl)-8,9,10,11-tetrahydro-7H-6,12-dioxa-1,3,9-triaza-cyclonona[b]naphthalen-4-yl]-amine (Compound 12)

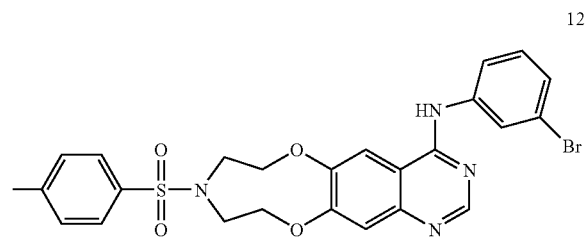

12

Following the same procedure as described in Example 1, Compound 12 was prepared and converted to the HCl salt: ES-MS m/z 555 (MH$^+$).

Example 5

(3-Bromo-phenyl)-(8,9-benzo-7,10-dihydro-6,11-dioxa-1,3-diaza-cycloocta[b]naphthalene-4-yl)-amine (Compound 13)

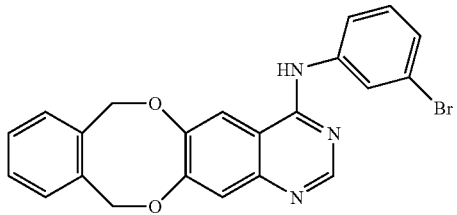

Following the same procedure as described in Example 1, Compound 13 was prepared and converted to its HCl salt. For HCl salt: $^1$H NMR (DMSO-d$_6$) δ 8.83 (s, 1H), 8.61 (s, 1H), 8.04 (s, 1H), 7.74 (d, J=7.7 Hz, 1H), 7.48–7.31 (m, 7H), 5.71 (s, 2H), 5.59 (s, 2H). ES-MS m/z 434 (MH$^+$).

Example 6

(3-Bromo-phenyl)-(8,9-dihydro-7H-6,10-dioxa-1,3-diaza-cyclohepta[b]naphthalen-4-yl)-amine (Compound 14)

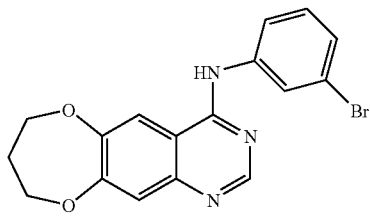

Following the same procedure as described in Example 1, Compound 14 was prepared and converted to the HCl salt (25 mg). For HCl salt: $^1$H NMR (DMSO-d$_6$) δ 8.90 (s, 1H), 8.44 (s, 1H), 8.07 (s, 1H), 7.76 (d, J=7.8 Hz, 1H), 7.52–7.45 (m, 2H), 7.42 (s, 1H), 4.45 (m, 2H), 4.36 (m, 2H), 2.28 (m, 2H). ES-MS m/z 372 (MH$^+$).

Example 7

(3-Chloro-4-fluoro-phenyl)-(7,8,10,11,13,14-hexahydro-6,9,12,15-tetraoxa-1,3-diaza-cyclododeca[b]naphthalen-4-yl)-amine (Compound 15)

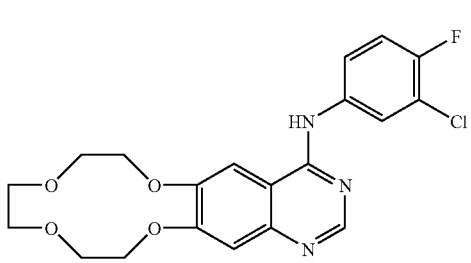

4-(3-Chloro-4-fluoro-phenylamino)-quinazoline-6,7-diol (61 mg, 0.2 mmol, prepared according to published procedures) was dissolved in DMF (8 mL). To this solution was added potassium carbonate (120 mg, 0.8 mmol). The mixture was heated slowly to 80° C., followed by slow addition of a DMF solution of tri(ethylene glycol)di-p-tosylate (92 mg, 0.2 mmol). The suspension was stirred at 80° C. overnight. DMF was removed in vacuo and the residue was purified by flash chromatography to give the product as a white solid: 58 mg (69%). $^1$H NMR (CDCl$_3$) δ 8.72 (s, 1H), 7.98 (d, 1H), 7.75 (s, 1H), 7.65 (s, 1H), 7.33 (d, 1H), 7.28 (s, 1H), 7.12 (s, 1H), 4.28 (s, 2H), 4.27 (s, 2H), 3.94 (s, 2H), 3.84 (s, 2H), 3.78 (s, 4H). ES-MS m/z 420 (MH$^+$).

Example 8

(3-Chloro-4-fluoro-phenyl)-(2,10-dioxa-6-thia-14,16-diaza-tricyclo[9.8.0.0$^{13,18}$]nonadeca-1-(11),12,14,16,18-pentaen-17-yl)-amine (Compound 16)

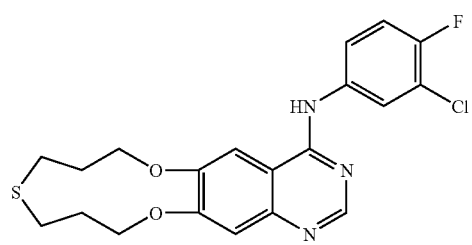

4-(3-Chloro-4-fluoro-phenylamino)-quinazoline-6,7-diol (61 mg, 0.2 mmol, prepared according to published procedures) was dissolved in DMF (8 mL). To this solution was added potassium carbonate (120 mg, 0.8 mmol). The mixture was heated slowly to 80° C., followed by slow addition of a DMF solution of 3,3'-Thiodipropyl di-p-tosylate (92 mg, 0.2 mmol). The suspension was stirred at 80° C. overnight. DMF was removed in vacuo and the residue was purified by flash chromatography to give the product as a white solid: 58 mg (69%). $^1$H NMR (CDCl$_3$) δ 8.75 (s, 1H), 8.00 (d, 1H), 7.24 (s, 1H), 7.26 (s, 1H), 7.42 (s, 1H), 7.30 (d, 1H), 7.25 (s, 1H), 4.40 (t, 4H), 4.75 (t, 2H), 3.40 (t, 2H), 2.55 (m, 2H), 2.23 (m, 2H); ES-MS m/z: 420 (MH$^+$).

Example 9

(3-Chloro-4-fluoro-phenyl)-(6,6-dioxo-2,10-dioxa-6-thia-14,16-diaza-tricyclo[9.8.0.0$^{13,18}$]nonadeca-1 (11),12,14,16,18-pentaen-17-yl)-amine (Compound 17)

(3-Chloro-4-fluoro-phenyl)-(2,10-dioxa-6-thia-14,16-diaza-tricyclo[9.8.0.0$^{13,18}$]nonadeca-1-(11),12,14,16,18-pentaen-17-yl)-amine (16, 140 mg, 0.33 mmol) was suspended in MeOH, to which was added a cloudy aqueous solution of oxone (monopersulfate compound) (820 mg, 1.33 mmol) at room temperature. The suspension was stirred and monitored by TLC which indicated that the reaction was completed in 4 h. The reaction mixture was poured into H$_2$O (10 mL), and extracted with EtOAc (3×15 mL). The organic layers were collected, dried and concentrated to give a pale yellow residue which was flash chromatographed to give the product as a white solid: 140 mg (93%). $^1$H NMR (CDCl$_3$) δ 8.75 (s, 1H), 8.00 (d, 1H), 7.24 (s, 1H), 7.26 (s, 1H), 7.42 (s, 1H), 7.30 (d, 1H), 7.25 (s, 1H), 4.40 (t, 4H), 4.75 (t, 2H), 3.40 (t, 2H), 2.55 (m, 2H), 2.23 (m, 2H); ES-MS m/z: 452 (MH$^+$).

Example 10

(3-Chloro-phenyl)-(7,8,10,11,13,14-hexahydro-6,9,12,15-tetraoxa-1,3-diaza-cyclododeca[b]naphthalen-4-yl)-amine (Compound 18)

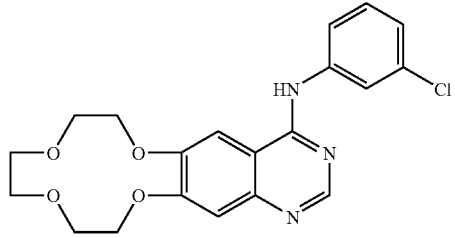

18

4-(3-Chloro-phenylamino)-quinazoline-6,7-diol (140 mg, 0.47 mmol, prepared according to published procedures) was dissolved in DMF (8 mL). To this solution was added potassium carbonate (280 mg, 2.0 mmol). The mixture was heated slowly to 80° C., followed by slow addition of a DMF solution of tri(ethylene glycol)di-p-tosylate (214 mg, 0.47 mmol). The suspension was stirred at 80° C. overnight. DMF was removed in vacuo and the residue was purified by flash chromatography to give the product as a white solid: 128 mg (68%). $^1$H NMR (CDCl$_3$) δ 8.50 (s, 1H), 7.98 (s, 1H), 7.97 (d, 1H), 7.75 (d, 1H), 7.32 (s, 1H), 7.30 (m, 2H), 7.27 (d, 1H), 4.46 (t, 2H), 4.17 (t, 2H), 3.85 (t, 4H), 3.75 (s, 4H).

Example 11

(3-Chloro-phenyl)-(2,10-dioxa-6-thia-14,16-diaza-tricyclo[9.8.0.0$^{13,18}$]nonadeca-1(11),12,14,16,18-pentaen-17-yl)-amine (Compound 19)

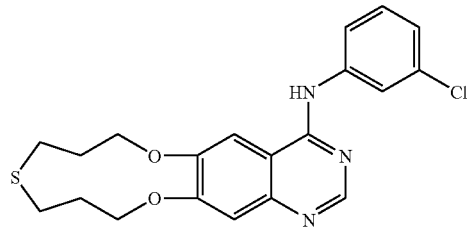

19

Following the same procedure as described in Example 8, compound 19 was prepared as a white solid: 46 mg (22%). $^1$H NMR (CDCl$_3$) δ 8.75 (s, 1H), 7.95 (s, 1H), 7.65 (d, 1H), 7.50 (s, 1H), 7.35 (t, 1H), 7.28 (s, 1H), 7.20 (s, 1H), 7.15 (d, 1H), 4.25 (m, 4H), 3.05 (t, 2H), 2.80 (t, 2H), 2.30 (m, 2H), 2.00 (m, 2H).

Example 12

(3-Chloro-phenyl)-(6,6-dioxo-2,10-dioxa-6-thia-14,16-diaza-tricyclo[9.8.0.0$^{13,18}$]nonadeca-1-(11),12,14,16,18-pentaen-17-yl)-amine (Compound 20)

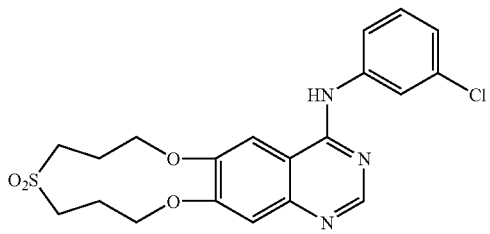

20

(3-Chloro-phenyl)-(2,10-dioxa-6-thia-14,16-diaza-tricyclo[9.8.0.0$^{13,18}$]nonadeca-1(11),12,14,16,18-pentaen-17-yl)-amine (19, 100 mg, 0.23 mmol) was suspended in MeOH, to which was added a cloudy aqueous solution of oxone (monopersulfate compound) (551 mg, 0.897 mmol) at room temperature. The suspension was stirred and monitored by TLC which indicated that the reaction was completed in 4 h. The reaction mixture was poured into H$_2$O (40 mL), and extracted with EtOAc (3×50 mL). The organic layers were collected, dried and concentrated to give a pale yellow residue which was recrystalized from EtOAc to give the product as an off-white solid: 31.5 mg (30%). $^1$H NMR (CDCl$_3$) δ 8.75 (s, 1H), 7.95 (s, 1H), 7.65 (d, 1H), 7.50 (s, 1H), 7.35 (t, 1H), 7.28 (s, 1H), 7.20 (s, 1H), 7.15 (d, 1H), 4.25 (m, 4H), 3.05 (t, 2H), 2.80 (t, 2H), 2.30 (m, 2H), 2.00 (m, 2H).

Example 13

(3-Bromo-phenyl)-(2,10-dioxa-6-thia-14,16-diaza-tricyclo[9.8.0.0$^{13,18}$]nonadeca-1(11),12,14,16,18-pentaen-17-yl)-amine (Compound 21)

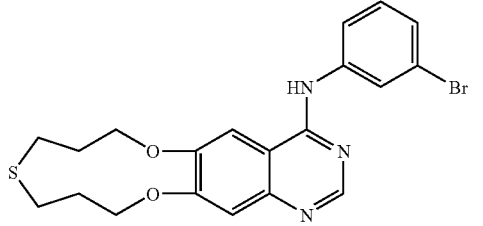

21

Following the same procedure as described in Example 8, compound 21 was prepared as a white solid: 165 mg (23%) $^1$H NMR (CD$_3$OD) δ 8.58 (s, 1H), 8.16 (s,1H), 8.11 (s, 1H), 7.81 (d, 1H), 7.72 (d, 1H), 7.48 (d, 1H), 7.35 (s, 1H), 7.30 (s, 1H), 4.35 (t, 4H), 3.70 (t, 2H), 3.40 (t, 2H), 2.40 (m, 2H), 2.15 (m, 2H);

Example 14

(3-Bromo-phenyl)-(6,6-dioxo-2,10-dioxa-6-thia-14,16-diaza-tricyclo[9.8.0.0$^{13,18}$]nonadeca-1(11),12,14,16,18-pentaen-17-yl)-amine (Compound 22)

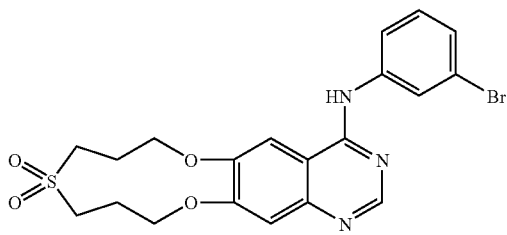

22

(3-Bromo-phenyl)-(2,10-dioxa-6-thia-14,16-diaza-tricyclo[9.8.0.0$^{13,18}$]nonadeca-1(11),12,14,16,18-pentaen-17-yl)-amine (21, 17.8 mg, 0.04 mmol) was suspended in MeOH, to which was added a cloudy aqueous solution of oxone (monopersulfate compound) (73 mg, 0.12 mmol) at room temperature. The suspension was stirred and monitored by TLC which indicated that the reaction was completed in 4 h. The reaction mixture was poured into H$_2$O (10 mL), and extracted with EtOAc (3×15 mL). The organic layers were collected, dried and concentrated to give a pale yellow residue which was recrystalized from EtOAc to give the product as an off-white solid: 8 mg (42%). $^1$H NMR (CD$_3$OD) δ 8.58 (s, 1H), 8.16 (s,1H), 8.11 (s, 1H), 7.81 (d, 1H), 7.72 (d, 1H), 7.48 (d, 1H), 7.35 (s, 1H), 7.30 (s, 1H), 4.35 (t, 4H), 3.70 (t, 2H), 3.40 (t, 2H), 2.40 (m, 2H), 2.15 (m, 2H); ES-MS m/z 478 (MH$^+$).

Example 15

(3-Ethynyl-phenyl)(7,8,10,11,13,14-hexahydro-6,9,12,15-tetraoxa-1,3-diazacyclododeca[b]naphthalen-4-yl)-amine (Compound 23)

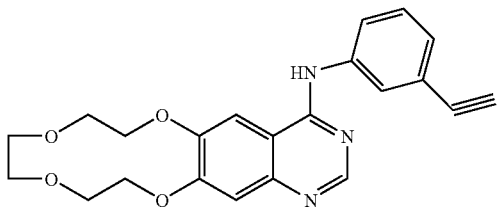

23

(3-Bromo-phenyl)-(7,8,10,11,13,14-hexahydro-6,9,12,15-tetraoxa-1,3-diaza-cyclododeca[b]naphthalen-4-yl)-amine (Compound 10) (10 mg, 0.5 mmol) was dissolved in DMF (10 mL). Tetrakis(triphenylphosphine) palladium (20 mg), trimethylsilylacetylene (70 microliter, 0.65 mmol), potassium carbonate (10 mg) and copper (I) iodide (5 mg) was added under nitrogen atmosphere. The reaction mixture was refluxed for about 3 h and then the reaction cooled and concentrated in vacuo, to afford a residue, which was flash chromotographed to provide a white solid (20 mg). ES-MS m/z 392 (MH$^+$).

Example 16

Formulation of a Hard Gel Capsule

As a specific embodiment of an oral composition, about 100 mg of the Compound 10 of Example 2 is formulated with sufficient finely divided lactose to provide a total amount of about 580 mg to about 590 mg to fill a size O hard gel capsule.

BIOLOGICAL ASSAYS

Compounds which potently inhibit the tyrosine kinase activity associated with the epidermal growth factor receptor (EGFR) may be identified and assessed by, for example, using the procedure described below:

Example 17

In Vitro EGFR Tyrosine Kinase Inhibition Assay

EGFR protein (2.4 ng/µl, 14.5 units/µg) was mixed with GST-Crk (32 ng/µl) in 25 µl kinase reaction buffer containing 1 µM cold ATP and 1 µCi $^{32}$P-γ-ATP. The mixture was incubated with inhibitors in ice for 10 minutes, then switched to 30° C. for another 20 minutes. After quenched by SDS sample buffer at 100° C. for 4 minutes, the protein mixture was separated by 10% SDS-PAGE gel. The dried gel was then exposed to Phosphorimager for quantification. The phosphorylated Crk was plotted against the concentration of inhibitor as shown in inhibition of tyrosine kinase activity of EGFR by inhibitors. The in vitro kinase assay indicates that the kinase activity of EGFR on Crk was inhibited by inhibitors disclosed with an IC$_{50}$ value of 2–500 nM.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entireties.

What is claimed is:

1. A compound having the structure

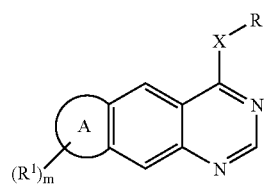

wherein A is a 9–15 membered, nonaromatic monocycle comprising at least 2 oxygen atoms and further comprising 0–3 heteroatoms selected from the group consisting of O, S and N;

R$^1$ is selected from the group consisting of hydrogen, halogen, substituted or unsubstituted C$_{1-8}$alkyl, substituted or unsubstituted C$_{2-8}$alkenyl, substituted or unsubstituted C$_{2-8}$alkynyl, substituted or unsubstituted aryl, substituted or unsubstituted heteroaryl, substituted or unsubstituted heterocyclyl;

m is an integer from 0 to 3;

X is selected from the group consisting of NR², CHR³, O, or S; wherein R² and R³ are each individually H or C$_{1-8}$alkyl; and R is selected from the group consisting of substituted or unsubstituted aryl, and substituted or unsubstituted heteroaryl, substituted or unsubstituted aryl-(C$_{1-3}$) alkyl, substituted or unsubstituted aryl-(C$_{3-7}$)cycloalkyl, and pharmaceutically acceptable salts thereof.

2. The compound of claim 1, wherein R¹ is selected from the group consisting of hydrogen, halogen, C$_{1-8}$alkyl, C$_{2-8}$alkenyl, C$_{2-8}$alkynyl, aryl, heteroaryl, heterocyclyl, (halo)$_{1-3}$(C$_{1-8}$)alkyl, hydroxy(C$_{1-8}$) alkyl, C$_{1-4}$alkoxy(C$_{1-8}$)alkyl, cyano(C$_{1-8}$)alkyl, aryl(C$_{1-8}$)alkyl, heteroaryl(C$_{1-8}$)alkyl, heterocyclyl(C$_{1-8}$)alkyl, (halo)$_{1-3}$(C$_{2-8}$)alkenyl, hydroxy(C$_{2-8}$)alkenyl, C$_{1-4}$alkoxy(C$_{2-8}$)alkenyl, cyano (C$_{2-8}$) alkenyl, aryl(C$_{2-8}$)alkenyl, heteroaryl (C$_{2-8}$) alkenyl, heterocyclyl(C$_{2-8}$)alkenyl, (halo)$_{1-3}$(C$_{2-8}$)alkynyl, hydroxy (C$_{2-8}$)alkynyl, C$_{1-4}$alkoxy(C$_{2-8}$)alkynyl, cyano(C$_{2-8}$)alkynyl, aryl(C$_{2-8}$)alkynyl, heteroaryl(C$_{2-8}$)alkynyl, and heterocyclyl(C$_{2-8}$)alkynyl.

3. The compound of claim 2, wherein any aryl, heteroaryl or heterocyclyl group within R¹ optionally bears one to three substituents independently selected from halogeno, trifluoromethyl, cyano, nitro, hydroxy, amino, carboxy, carbamoyl, (C$_{1-4}$)alkyl, (C$_{2-4}$)alkenyl, (C$_{2-4}$)alkynyl, (C$_{1-4}$)alkoxy.

4. The compound of claim 1, wherein R¹ is selected from the group consisting of hydrogen, halogen, C$_{1-4}$alkyl, C$_{2-4}$alkenyl, C$_{2-4}$alkynyl, aryl, heteroaryl, heterocyclyl, (halo)$_{1-3}$(C$_{1-4}$)alkyl, hydroxy(C$_{1-4}$)alkyl, C$_{1-4}$alkoxy(C$_{1-4}$) alkyl, cyano(C$_{1-4}$) alkyl, heteroaryl(C$_{1-4}$)alkyl, heterocyclyl (C$_{1-4}$)alkyl, and wherein any aryl, heteroaryl or heterocyclyl group within R¹ optionally bears one to three substituents independently selected from halogen, trifluoromethyl, cyano, nitro, hydroxy, amino, carboxy, carbamoyl, (C$_{1-4}$) alkyl, (C$_{2-4}$)alkenyl, hydroxy(C$_{2-4}$)alkynyl, (C$_{1-4}$)alkoxy.

5. The compound of claim 1, wherein said aryl or heteroaryl group of R are each optionally substituted with one to three substituents independently selected from the group consisting of halogen, C$_{1-8}$alkyl, C$_{2-8}$alkenyl, C$_{2-8}$alkynyl, cyano, nitro, hydroxy, amino, carboxy, carbamoyl, C$_{1-8}$alkoxy, C$_{2-8}$alkenyloxy, C$_{2-8}$alknyloxy, C$_{1-8}$alkylthio, C$_{1-8}$alkylsuiphinyl, C$_{1-8}$alkylsulphonyl, C$_{1-8}$alkoxycarbonyl, N-(C$_{1-8}$alkyl)carbamoyl, N,N-di-(C$_{1-8}$alkyl)carbamoyl, (halo)$_{1-3}$(C$_{1-8}$)alkyl-, (halo)$_{1-3}$(C$_{1-8}$)alkoxy-, hydroxy(C$_{1-8}$) alkyl, C$_{1-4}$alkoxy(C$_{1-8}$)alkyl, cyano(C$_{1-8}$)alkyl, amino(C$_{1-8}$) alkyl, aryl(C$_{1-8}$)alkyl, -heteroaryl(C$_{1-8}$)alkyl, heterocyclyl, heterocyclyl(C$_{1-8}$)alkyl, C$_{2-8}$alkanoyl, C$_{2-8}$alkanoyloxy, C$_{2-8}$alkanoylamino, C$_{3-8}$alkenoylamino, C$_{3-8}$alkynoylamino, N-(C$_{1-8}$alkyl)sulphamoyl, N.,N-di-(C$_{1-8}$alkyl) sulphamoyl, C$_{1-8}$alkanesulphonylamino, or from a group of the formula:

—Y—R⁴ wherein Y is selected from O, S, N(R⁵), SO, SO$_2$, CO, CON(R⁵), N(R⁵)CO, SO$_2$N(R⁵), N(R⁵)SO$_2$, wherein R⁵ is hydrogen or (C$_{1-4}$)alkyl, and R⁴ is halogeno-(C$_{1-8}$)alkyl, hydroxy-(C$_{1-8}$)alkyl, (C$_{1-4}$)alkoxy-(C$_{1-8}$)alkyl, cyano-(C$_{1-8}$) alkyl, amino-(C$_{1-8}$) alkyl, (C$_{1-8}$)alkylamino-(C$_{1-8}$)alkyl or di-[(C$_{1-8}$)alkyl]amino-(C$_{1-8}$)alkyl, aryl, aryl-(C$_{1-8}$)alkyl, heteroaryl, heteroaryl-(C$_{1-8}$)alkyl, heterocyclyl or heterocyclyl-(C$_{1-8}$)alkyl.

6. The compound of claim 5, wherein said amino or amino(C$_{1-8}$)alkyl within a substituent on R is substituted with two substituents independently selected from the group consisting of hydrogen, C$_{1-8}$alkyl, C$_{2-8}$alkenyl, and C$_{2-8}$alkynyl; and wherein any aryl, heteroaryl or heterocyclyl group within a substituent on R optionally bears one to three substituents independently selected from the group consisting of halogen, trifluoromethyl, cyano, nitro, hydroxy, amino, carboxy, carbamoyl, (C$_{1-2}$)alkyl, (C$_{2-8}$) alkenyl, (C$_{2-8}$)alkynyl, and (C$_{1-8}$)alkoxy.

7. The compound of claim 1, wherein said aryl or heteroaryl group of R are each optionally substituted with one to three substituents independently selected from the group consisting of halogen, C$_{1-8}$alkyl, C$_{2-8}$alkenyl, cyano, nitro, hydroxy, amino, carboxy, C$_{1-8}$alkoxy, C$_{2-8}$alkenyloxy, C$_{2-8}$alknyloxy, C$_{1-8}$alkylthio, aryl, aryl(C$_{1-8}$)alkyl, heteroaryl, heteroaryl(C$_{1-8}$)alkyl, heterocyclyl, heterocyclyl (C$_{1-8}$)alkyl and (C$_{1-3}$) alkylenedioxy.

8. The compound of claim 1, wherein R is selected from substituted or unsubstituted aryl, and substituted or unsubstituted heteroaryl.

9. The compound of claim 1, wherein R is substituted or unsubstituted phenyl.

10. The compound of claim 1, wherein m is 0 to 2.

11. The compound of claim 1, wherein X is NR²; and R² is H or C$_{1-4}$alkyl.

12. The compound of claim 1 selected from the group consisting of:

(3-Bromo-phenyl)-(7,8,10,11-tetrahydro-6,9,12-trioxa-1,3-diaza-cyclonona[b]naphthalen-4-yl)-amine;

(3-Bromo-phenyl)-(7,8,10,11,13,14-hexahydro-6,9,12,15-tetraoxa-1,3-diaza-cyclododeca[b]naphthalen-4-yl)amine;

(3-Bromo-phenyl)-(2,5,8,11,14pentaoxa-18,20-diaza-tricyclo[13.8.0.0$^{17,22}$]tricosa-1(15),16,18,20,22-pentaen-21yl)-amine;

(3-Bromo-phenyl)-[9-(toluene-4-sulfonyl)-8,9,10,11-tetrahydro-7H-6,12-dioxa-1,3,9-triaza-cyclonona[b]naphthalen-4-yl]-amine;

(3-Bromo-phenyl)-(8,9-benzo-7,10-dihydro-6,11-dioxa-1,3-diaza-cycloocta[b]naphthalene-4-yl)-amine;

(3-Chloro-4-fluoro-phenyl)-(7,8,10,11,13,14-hexahydro-6,9,12,15-tetraoxa-1,3-diaza-cyclododeca[b]naphthalen-4-yl)-amine;

(3-Chloro-4-fluoro-phenyl)-(2,10dioxa-6-thia-14,16-diaza-tricyclo[9.8.0.0$^{13,18}$]nonadeca-1-(11),12,14,16,18-pentaen-17-yl)-amine;

(3-Chloro-4-fluoro-phenyl)-(6,6-dioxo-2,10-dioxa-6-thia-14,16-diaza-tricyclo[9.8.0.0$^{13,18}$]nonadeca-1(11),12,14,16,18-pentaen-17-yl)-amine;

(3Chloro-phenyl)-(7,8,10,11,13,14-hexahydro-6,9,12,15-tetraoxa-1,3-diaza-cyclododeca[b]naphthalen-4-yl)-amine;

(3-Chloro-phenyl)-(2,10-dioxa-6-thia-14,16-diaza-tricyclo[9.8.0.0$^{13,18}$]nonadeca-1(11),12,14,16,18-pentaen-17-yl)amine;

(3Chloro-phenyl)-(6,6-dioxo-2,10-dioxa-6thia-14,16-diaza-tricyclo[9.8.0.0$^{13,18}$]nonadeca-1-(11),12,14,16,18-pentaen-17-yl)-amine;

(3-Bromo-phenyl)-(2,10-dioxa-6-thia-14,16-diaza-tricyclo[9.8.0.0$^{13,18}$]nonadeca-1(11),12,14,16,18-pentaen-17-yl)-amine;

(3-Bromo-phenyl)-(6,6-dioxo-2,10-dioxa-6-thia-14,16-diaza-tricyclo[9.8.0.0$^{13,18}$]nonadeca-1(11),12,14,16,18-pentaen-17-yl)-amine;

(3-Ethynyl-phenyl)-(7,8,10,11,13,14-hexahydro-6,9,12,15-tetraoxa-1,3-diazacyclododeca[b]naphthalen-4-yl)-amine.

13. The compound of claim 1, wherein said pharmaceutically acceptable salts are acidic/anionic or basic/cationic salts.

14. A pharmaceutical composition, comprising:
the compound of claim 1; and
a pharmaceutically acceptable carrier.

15. The pharmaceutical composition of claim 14, wherein said pharmaceutically acceptable carrier is selected from the group consisting of water, gelatin, lactose, starch, magnesium stearate, talc, plant oils, gums, alcohol, Vaseline, and combinations thereof.

16. A method of treating a patient suffering from EGFR tyrosine kinase-mediated disorders, selected from the group consisting of lung cancer, squamous cell cancer, breast cancer, prostate cancer, colorectal cancer, gynecological or thyroid cancers, and combinations thereof, the method comprising the step of administering to said patient a therapeutically effective amount of the compound of claim 1.

* * * * *